United States Patent
Ward

(10) Patent No.: US 9,498,641 B2
(45) Date of Patent: Nov. 22, 2016

(54) FAT REDUCING DEVICE AND METHOD UTILIZING OPTICAL EMITTERS

(71) Applicant: Terry Ward, Orlando, FL (US)

(72) Inventor: Terry Ward, Orlando, FL (US)

(73) Assignee: Blue Water Innovations, LLC, Charlestown, Nevis (*) Notice: Subject to any disclaimer, the term of this patent is extended or adjusted under 35 U.S.C. 154(b) by 229 days.

(21) Appl. No.: 13/782,377

(22) Filed: Mar. 1, 2013

(65) Prior Publication Data

US 2014/0249607 A1    Sep. 4, 2014

Related U.S. Application Data

(60) Provisional application No. 61/606,628, filed on Mar. 5, 2012.

(51) Int. Cl.
*A61N 5/06* (2006.01)
*A61B 18/00* (2006.01)

(52) U.S. Cl.
CPC ... *A61N 5/0613* (2013.01); *A61B 2018/00464* (2013.01); *A61N 2005/0642* (2013.01); *A61N 2005/0652* (2013.01); *A61N 2005/0662* (2013.01)

(58) Field of Classification Search
CPC .. A61N 5/0613; A61N 5/0616; A61N 5/062; A61N 5/0626; A61N 5/0627; A61N 2005/0636; A61N 2005/064; A61N 2005/0642; A61N 2005/0652; A61N 2005/0654; A61N 2005/0658
USPC ............ 607/88–91, 96, 100; 606/9–12
See application file for complete search history.

(56) References Cited

U.S. PATENT DOCUMENTS

| 5,143,063 | A | 9/1992 | Felner |
| 5,507,790 | A | 4/1996 | Weiss |
| 6,602,275 | B1* | 8/2003 | Sullivan ......................... 607/88 |
| 6,645,162 | B2 | 11/2003 | Friedman et al. |
| 7,351,252 | B2 | 4/2008 | Altshuler et al. |
| 7,364,583 | B2* | 4/2008 | Rose ............................... 607/88 |
| 7,993,382 | B2 | 8/2011 | Shanks et al. |
| 8,317,781 | B2* | 11/2012 | Owens ................. A61B 18/203 606/10 |
| 8,366,756 | B2 | 2/2013 | Tucek et al. |
| 9,044,595 | B2* | 6/2015 | Araya ................. A61N 5/0613 |
| 2004/0044384 | A1* | 3/2004 | Leber ................... A61N 5/0619 607/88 |
| 2006/0064144 | A1* | 3/2006 | Chen et al. ....................... 607/90 |
| 2007/0197884 | A1 | 8/2007 | Bornstein |
| 2008/0119912 | A1* | 5/2008 | Hayes ............................ 607/88 |
| 2008/0275533 | A1* | 11/2008 | Powell ........................... 607/88 |
| 2013/0268035 | A1* | 10/2013 | Araya et al. .................... 607/94 |

OTHER PUBLICATIONS

Lipo-Light.Com; Lipo-Light.Com/Beauty-Salon-News-Nov-Dec-2011. (Nov.-Dec. 2011). http://lipo-light.com/Beauty-Salon-News-Nov-Dec-2011.pdf.
International Search Report and Written Opinion, PCT/US13/28824.
Uniform Case No. 482012CA013906A001OX Ninth Judicial Circuit Court of Florida, Orange County, Div 43 Araya, Heidi vs. Ward, Terry J et al.
U.S. Appl. No. 13/784,166, filed after the present application, by Heidi Araya Plaintiff in the above noted case.

* cited by examiner

*Primary Examiner* — Ahmed Farah
(74) *Attorney, Agent, or Firm* — Jason T. Daniel, Esq.; Daniel Law Offices, P.A.

(57) ABSTRACT

A fat reducing device and method utilizing optical emitters includes an array housing a plurality of optical emitters which are positioned to produce an optical output directed to a recipient, and a controller for instructing an operation of the array. The optical output being generated by a plurality of LED's cumulatively producing red light at approximately 635 nm, and at approximately 40,000 Lux, measurable at the array. The method includes reducing the lipid content of subcutaneous adipocytes using the optical emitting device, by delivering red light at approximately 313.6 Lux at a wavelength of approximately 635 nm for between 1 and 8 minutes, resulting in a total delivery of 2.88 Joules to the subcutaneous adipocytes of the target area of the recipient.

9 Claims, 9 Drawing Sheets

1

FAT REDUCING DEVICE AND METHOD UTILIZING OPTICAL EMITTERS

CROSS-REFERENCE TO RELATED APPLICATIONS

This application claims the benefit of U.S. application Ser. No. 61/606,628 filed on 5 Mar. 2012, the contents of which are incorporated herein by reference.

TECHNICAL FIELD

The present invention relates generally to the field of weight loss, and more particularly, to a device and method for reducing body fat utilizing optical emitters.

BACKGROUND

The statements in this section merely provide background information related to the present disclosure and may not constitute prior art.

Weight loss products such as pharmaceuticals, holistic treatments and/or diet plans, for example, are a multi-billion dollar a year industry dedicated to assisting consumers in the reduction of unwanted fat and weight gain. The majority of these products function to reduce the feelings of hunger or reduce the absorption of nutrition taken in by the dieter. While these products may be useful for a short time, studies have shown that continued use often results in diminishing returns. To this end, it has long been held that the best way to reduce fat deposits without surgical and/or medical devices is through behavior modification that includes proper diet and exercise. In many cases, however, there is a high rate of recidivism and noncompliance when the dieter reverts to his or her former eating and lifestyle patterns. As such, long term success is only moderately successful, and short term weight loss is typically followed by weight gain.

As a result of the above, many dieters turn to surgical methods, such as liposuction, for example, in order to achieve a noticeable result in a shorter period of time. Although surgical methods can more quickly obtain measurable results, in terms of fat removal, the act of removing adipocytes (i.e., fat cells) from a localized subcutaneous body portion often results in dysmorphic lipid (i.e., fat) accumulation if the dieter gains weight in the future. Additionally, surgery is a painful invasive procedure which exposes the patient to health risks such as trauma and infection. Moreover, even when performed properly, surgical procedures such as liposuction can cause damage to the surrounding tissue, nerves and skin.

Several less invasive medical approaches include the utilization of radio frequencies, ultrasound and/or cryogenics to kill localized fat cells which can then be metabolized by the body. Although less invasive, by removing or killing the fat cells, each of these approaches also results in future dysmorphic fat accumulation and often causes damage to surrounding tissues. Additionally, as the final results of these methods may take up to four months to see, they do not satisfy the need for a more immediate result.

More recent approaches have centered on the use of laser radiation to affect the fat cells of the human body. In her study "Changes in absorbance of monolayer of living cells induced by laser radiation at 633, 670 and 820 nm" reported in Selected Topics in Quantum Electronics. 2001; 7 (6): 982-988, Dr. Karu's results obtained evidence that cytochrome coxidase becomes more oxidized (which means that the oxidative metabolism is increased) due to irradiation at all wavelengths used. The results of that experiment supports the suggestion (Karu, Lasers Life Sci., 2:53, 1988) that the mechanism of low-power laser therapy at the cellular level is based on the electronic excitation of chromophores in cytochrome c oxidase which modulates a redox status of the molecule and enhances its functional activity.

To this end, several devices and methods have been described in the art and include U.S. Patent Application Publication No. 2007/0197884 to Bornstein, which discloses a fat reduction approach. U.S. Pat. No. 7,993,382 to Shanks et al. discloses a fat reduction method using external laser radiation and niacin. U.S. Pat. No. 7,351,252 to Altshuler et al. discloses a method and apparatus for photothermal treatment of tissue at depth. This method may cause heat damage to the epidermis. U.S. Pat. No. 6,645,162 to Friedman et al.; U.S. Pat. No. 5,507,790 to Weiss; and U.S. Pat. No. 5,143,063 to Fellner each disclose methods that allow the fat cell to be destroyed, but will require significant recovery time.

Background FIG. 1 illustrates one example of the distribution output pattern of a conventional laser device used to reduce fat. As shown, the laser output pattern comprises an elongated beam 2 having a fixed width W that is typically between 2 and four inches. The beam is directed onto the skin 1 of a patient 5 at a location where fat is present. This beam 2 is then rotated, see arrow a, about a central axis 3 for a predetermined period of time. When utilized in this manner, the area of skin being treated 1 does not receive uniform coverage of the laser, as the central axis 3 remains generally fixed, while the remainder of the beam 2 covers a constantly moving area. Additionally, owing to the small size of the beam, multiple lasers must be used to treat larger target areas such as the stomach, thighs, and buttocks, for example. Such a procedure further exposes the patient to less than desirable results, as one of the lasers may be more or less powerful than another, thereby causing uneven results. Because all of the energy of the laser is focused on a very small area at any point in time, the power of the laser must be very low to avoid permanently damaging the cells, resulting in a far less effective outcome than could otherwise be achieved.

Additionally, the safety of the patient and the device operator are a concern when utilizing laser products. To this end, the conventional laser devices are capable of concentrating a destructive tightly-focused beam of light on the retina (up to 60,000 Watts per cm), which can cause permanent damage to the eye. As will be described below, the present invention simply cannot do that. The potential to damage the retina is 504,515 times greater with conventional lasers than with the device of the presently claimed invention which can concentrate only 0.1 Watts per cm.

Owing to the demanding and exacting power and wavelength requirements described above, experts in the field of lasers and photonics have expressed doubts about the ability to remove lipids from subcutaneous adipocytes utilizing other, less powerful forms of light. Nonetheless, there has been one recent attempt to utilize alternative lighting elements to reduce unwanted fat deposits. Lipo-Light is a commercially available product that is produced by Innovate Photonics Ltd. The product utilizes six paddles each containing 25 LEDs that produce a total of 2.4 watts at full fluency (combined effect from all 6 paddles). The device requires that each of the paddles be strapped directly to the skin of a patient for at least 20 minutes, and purports to achieve "slimming and toning" results.

However, by requiring each of the paddles be placed directly against the skin, the medical practitioner is not able to directly view the interaction of the device paddles with the skin, and may not be able to quickly or adequately respond to an unanticipated reaction by the patient, such as burning, or an allergic reaction, for example. Moreover, the direct application of the paddles results in a patchwork approach wherein gaps between the paddles are not exposed to the light.

Accordingly, there remains a need for a device capable of reducing the lipid content of adipocytes within the human body that does not suffer from the drawbacks of the devices described above, and is capable of uniformly illuminating the skin over a large area and does not require an unsanitary transfer between patients that are inherent in the conventional paddle systems.

SUMMARY OF THE INVENTION

The present invention is directed to a fat reducing device and method utilizing optical emitters. One embodiment of the present invention can include an array housing a plurality of optical emitters which can be positioned to produce an optical output directed to a recipient, and a controller for instructing an operation of the array. The optical output can be generated by a plurality of LED's cumulatively producing red light at approximately 635 nm, and at approximately 40,000 Lux, measurable at the array.

Another embodiment of the present invention can include components for modulating the power delivered to the array based on a reference waveform created internally or via an external device.

Yet another embodiment of the present invention can include a method of reducing lipid content of subcutaneous adipocytes using the optical emitting device. The method including delivering red light at approximately 313.6 Lux at a wavelength of approximately 635 nm for between 1 and 8 minutes, resulting in a total delivery of 2.88 Joules to the subcutaneous adipocytes of the target area of the recipient.

BRIEF DESCRIPTION OF THE DRAWINGS

Presently preferred embodiments are shown in the drawings. It should be appreciated, however, that the invention is not limited to the precise arrangements and instrumentalities shown.

FIGS. 6a and 6b are diagrams of the modulation input signal and the rectified input signal, respectively, in the controller of FIG. 4a.

DETAILED DESCRIPTION OF THE INVENTION

Figure 1:
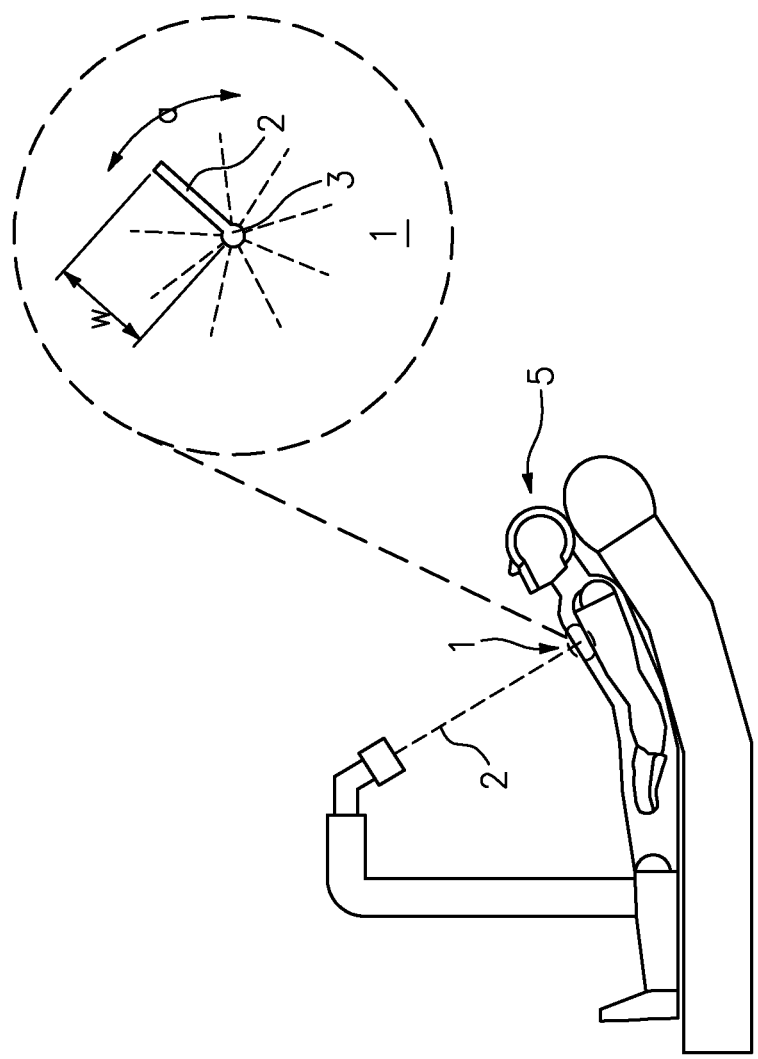
FIG. 1 is a perspective view of a laser device in accordance with background art.

While the specification concludes with claims defining the features of the invention that are regarded as novel, it is believed that the invention will be better understood from a consideration of the description in conjunction with the drawings. As required, detailed embodiments of the present invention are disclosed herein; however, it is to be understood that the disclosed embodiments are merely exemplary of the invention which can be embodied in various forms. Therefore, specific structural and functional details disclosed herein are not to be interpreted as limiting, but merely as a basis for the claims and as a representative basis for teaching one skilled in the art to variously employ the inventive arrangements in virtually any appropriately detailed structure. Further, the terms and phrases used herein are not intended to be limiting but rather to provide an understandable description of the invention.

As will be described throughout this document, a fat reducing device and method utilizing optical emitters can act to decrease the lipid content of adipocytes without permanent or adverse effects on the cells and their surrounding tissues. The device can illuminate the epidermis, dermis and underlying adipose tissue by applying light/radiation from an array of optical emitters at a target wavelength causing a photochemical reaction that stimulates specific cellular enzymatic processes, such as lipolysis, stimulation of production of collagen, elastin, leptin, and adiponectin. Modulation is not required, but may enhance results.

As described herein, an "optical emitter" can include virtually any type of light emitting device including, but not limited to, light emitting capacitors, light emitting diodes (LEDs) and/or super-luminous light emitting diodes, for example, that are capable of individually and/or jointly creating optical emissions of light/radiation at a target wavelength.

Through extensive research, testing and development, the inventor has discovered that subcutaneous adipocytes will expel their lipid content when receiving red light at approximately 313.6 Lux at a wavelength of approximately 635 nm for between 1 and 8 minutes, resulting in a total delivery of 2.88 Joules. Of course, as human skin and the underlying tissue reflects and/or absorbs light, it is necessary that the measurable light/radiation output leaving the array be greater than the amount that is desired to make contact with the subcutaneous adipocytes of the recipient.

Accordingly, and as described herein, a "target wavelength" and an "optical output" shall be used interchangeably to describe the measurable light/radiation output of the array that is sufficient to apply about 313.6 Lux subcutaneously to the adipocytes of the target area of a human recipient for a total delivered energy of 2.88 Joules (typically requiring an exposure duration of between 1 and 8 minutes).

In one embodiment, this measurable optical output (measurable at the array itself) shall include an output of red light at approximately 635 nm, at approximately 40,000 Lux. When the array is positioned at a distance of between 1 and 8 inches from the skin/target area of the recipient, approximately 313.6 Lux (of the 40,000 produced by the array) can penetrate the skin and can be delivered to the subcutaneous adipocytes. Of course, the distance and time can be slightly adjusted to account for the inherent variances of skin makeup from one person to another. In either instance, upon receiving the 313.6 Lux at 635 nm for approximately 1 to 8 minutes, the desired energy of 2.88 Joules will be delivered thereby causing the lipid content to be expelled from the adipocytes without causing cellular damage.

In addition to reducing lipid content within subcutaneous adipocytes, the inventor has seen promising results in the reduction of visceral fat. Visceral fat is also known as intra-abdominal fat, and is located inside the abdominal cavity, packed between the organs. To this end, when the array is positioned at a distance of between 1 and 2 inches from the skin/target area, the requisite 313.6 Lux at 635 nm for approximately 12-16 minutes, the desired energy of 2.88 Joules can be delivered to the visceral fat.

As is known to those of skill in the art, unlike lasers, which are monochromatic and can be manufactured to produce an identifiable and constant wavelength, LEDs have a distribution of colors. Therefore, LEDs have a spectrum distribution as opposed to a fixed wavelength that takes into account light output and color. As such, current manufacturing techniques may be unable to provide a plurality of LEDs which can each deliver an exact peak or dominant wavelength at exactly 635 nm on a consistent basis. Therefore, when utilizing LEDs, within the below described array, the optical output can include an output spectrum approaching or as close to 635 nm as possible so as to deliver about 313.6 Lux subcutaneously. Such a feature can be accomplished by individually testing the output of each LED prior to positioning the light within the array.

Accordingly, when operating in the target wavelength i.e. at a suitable power dosimetry, e.g., from about 50 mW/cm2 to about 110 mW/cm2, the device can stimulate an increase in biochemical processes, and in addition, emptying of contents of adipocytes over a large portion of a person's body.

Figure 3A:
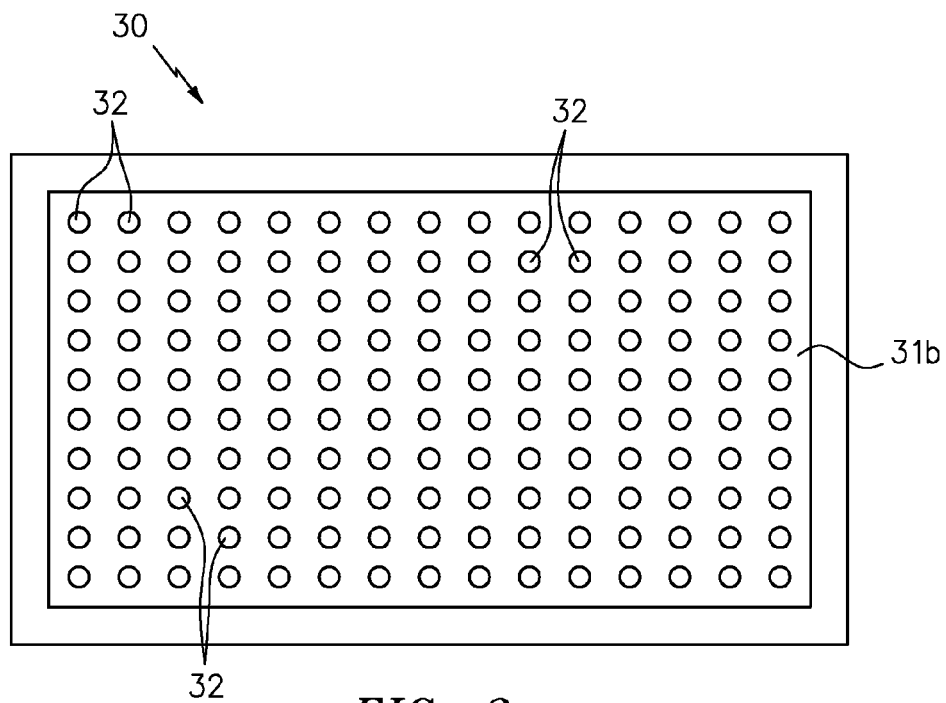
FIG. 3a is a bottom side view of the array for use with the fat reducing device utilizing optical emitters in accordance with one embodiment of the invention.

In the device of the present disclosure, it is normally possible to decrease the lipid content of treated adipocytes in a noticeable manner within minutes of treatment. Moreover, by utilizing an array of optical emitters, the device of the present disclosure can uniformly treat a much larger target area. The target area of the array described below in FIG. 3a, is approximately 23" by 17," and does not requiring cooling of tissue surfaces after use, or cause damage to the cells, as compared with conventional treatment devices.

Accordingly, the presently claimed invention can allow a recipient to experience the many biological processes that take place in tissues that have been shown to respond to light in the 630-640 nm wavelength range. One of these processes is the enhancement of ATP production in the mitochondria, which provides more energy substrate for cellular healing and tissue recovery post injury. The target wavelength has also been shown to decrease inflammatory mediators in wounds and increase endogenous endorphin release.

Turning now to the drawings, where identical reference numerals are used for like elements of the invention or elements of like function. For the sake of clarity, only those reference numerals are shown in the individual figures which are necessary for the description of the respective figure. For purposes of this description, the terms "upper," "bottom," "right," "left," "front," "vertical," "horizontal," and derivatives thereof shall relate to the invention as oriented in FIG. 2.

Figure 2:
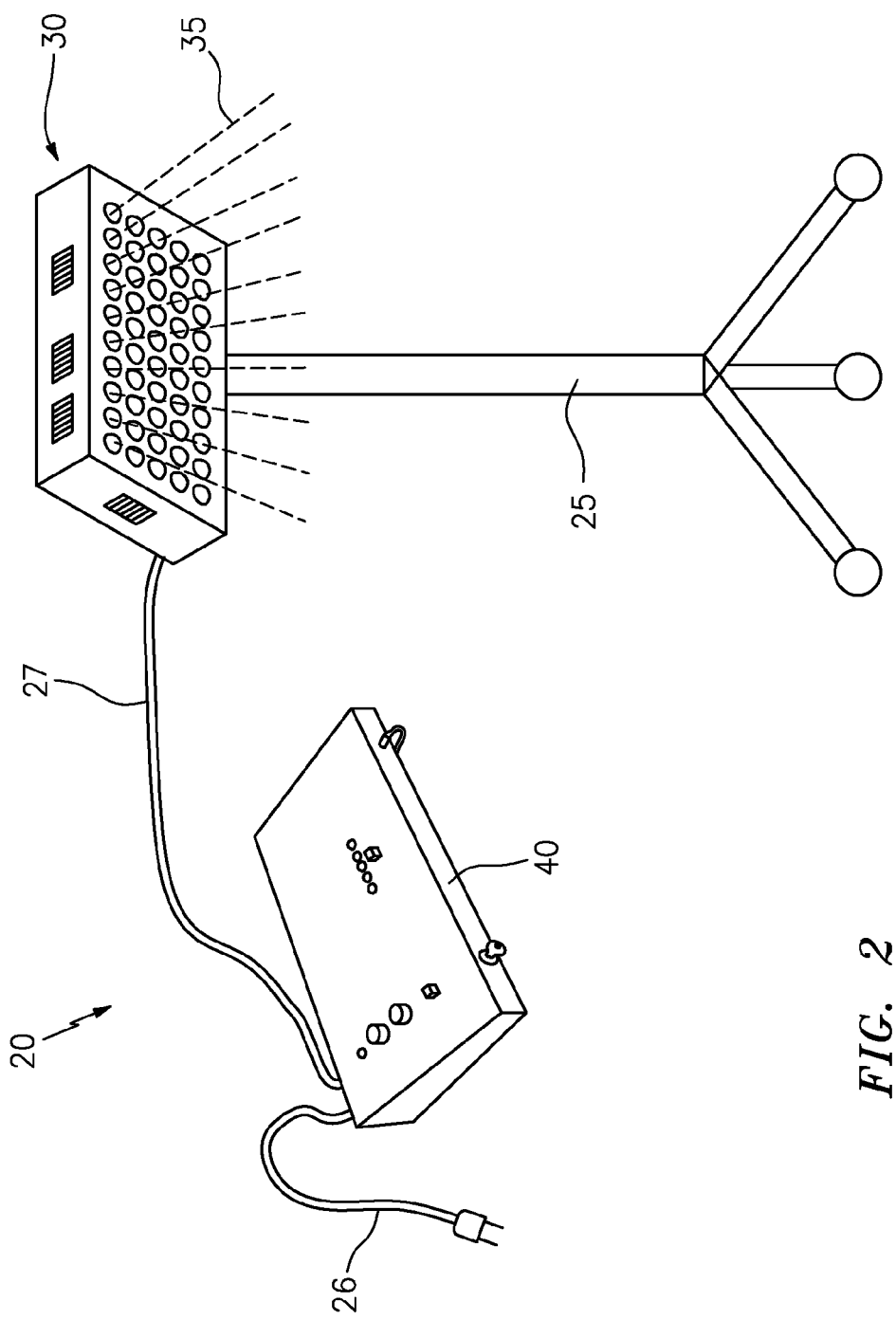
FIG. 2 is a perspective view of the fat reducing device utilizing optical emitters in accordance with one embodiment of the invention.

FIG. 2 illustrates one embodiment of a fat reducing device utilizing optical emitters that is useful for understanding the inventive concepts disclosed herein. As shown, the device 20 can include an array of optical emitters 30 (array) which can operate to produce light/radiation 35 at a target wavelength when instructed by a controller 40. A multi-positional stand 25 can be secured to array 30 for precise alignment and positioning over a recipient. The controller 40 can include a power cable 26 for mating with a conventional 120V AC power source, and a second cable 27 can be provided to supply power from the controller 40 to the array 30.

Figure 3B:
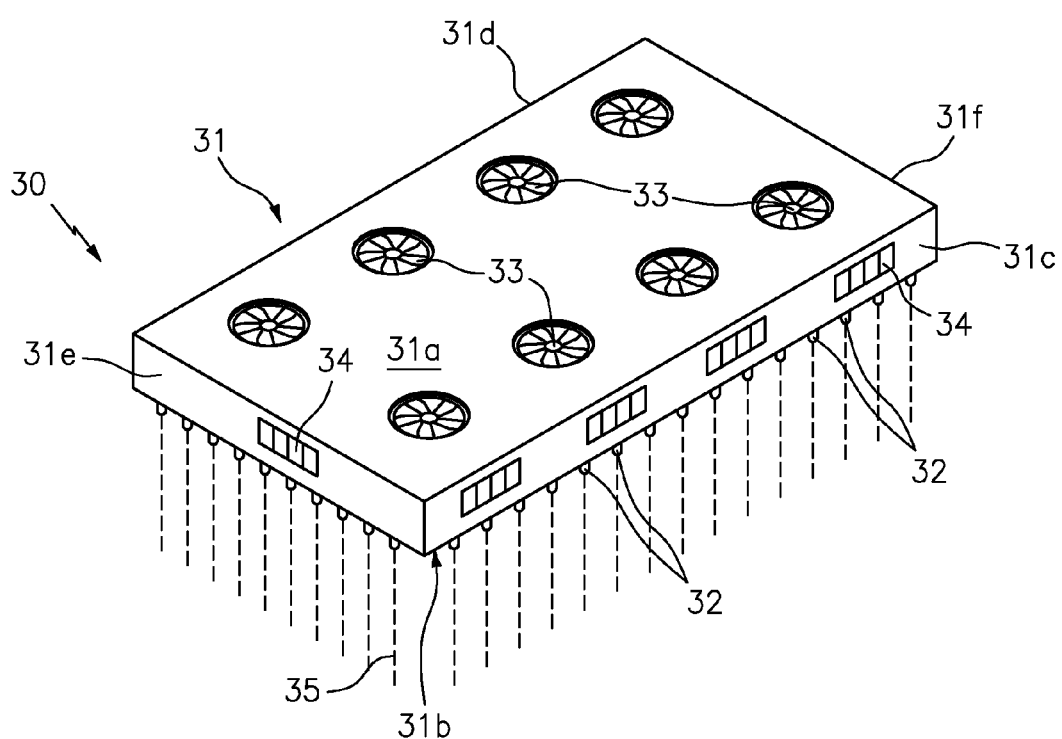
FIG. 3b is a perspective side view of the array of the fat reducing device utilizing optical emitters in accordance with one embodiment of the invention.

FIGS. 3a and 3b illustrate one embodiment of a suitable array 30. The array can include a generally rectangular main body having a top surface 31a, a bottom surface 31b, a front surface 31c, a back surface 31d and opposing side surfaces 31e and 31f, each forming a generally hollow interior space. A plurality of optical emitters 32 are positioned within the main body 31 so as to allow the emissions therefrom to be directed outward from the bottom surface 31b. Additionally, a plurality of ventilation devices such as fans 33 heat syncs (not shown) and/or air vents 34 can be provided on or within the main body to allow proper air ventilation.

In one preferred embodiment, the main body can be constructed from metal, and the plurality of optical emitters 32 can include 150 2-Watt LEDs that receive 120V AC power from the cable 27, at the discretion of the controller 40. When power is provided to the array 30, the plurality of emitters 32 can produce an optical output sufficient to ensure about 313.6 Lux and can be subcutaneously delivered to the adipocytes of the target area of the recipient in order to remove the stored lipids.

Although described above as including a specific shape, construction material, type and number of light emitting sources, this is for illustrative purposes only, as those of skill in the art will recognize that many different combinations and types of optical emitters and/or main body shapes and construction materials can also be utilized to achieve the desired optical output described above. Moreover, although illustrated as protruding out from the main body, the optical emitters 32 can also be flush mounted in accordance with known manufacturing techniques.

Figure 4A:
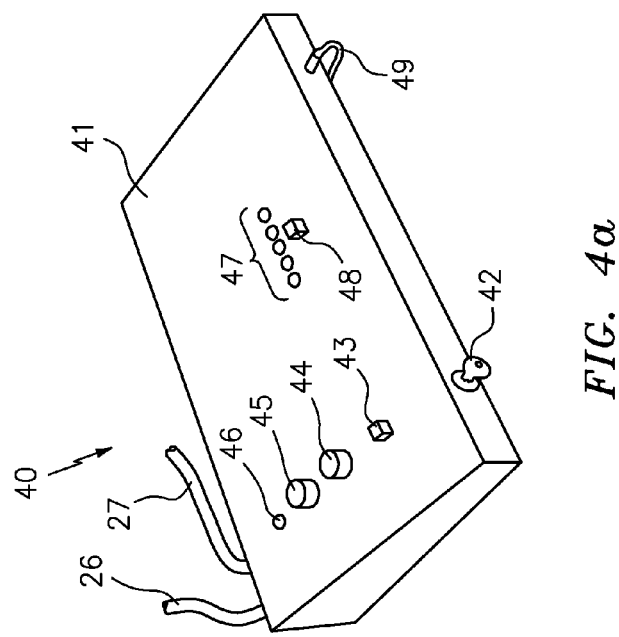
FIG. 4a is a perspective view of the controller of the fat reducing device utilizing optical emitters in accordance with one embodiment of the invention.

FIG. 4a illustrates an exterior view of one embodiment of the controller 40. As shown, the controller can include a main body 41 having a plurality of user controls and/or interface devices secured thereon. These devices can include, for example, a key switch 42, a stop button 43, a volume selector 44, an exposure time selector 45 an array indicator 46, a modulation signal strength indicator (VU meter) 47, a start button 48 and a signal input jack 49. Of course any number of other interface devices can also be provided, as necessary or desired to control the functionality of the array.

Figure 5A:
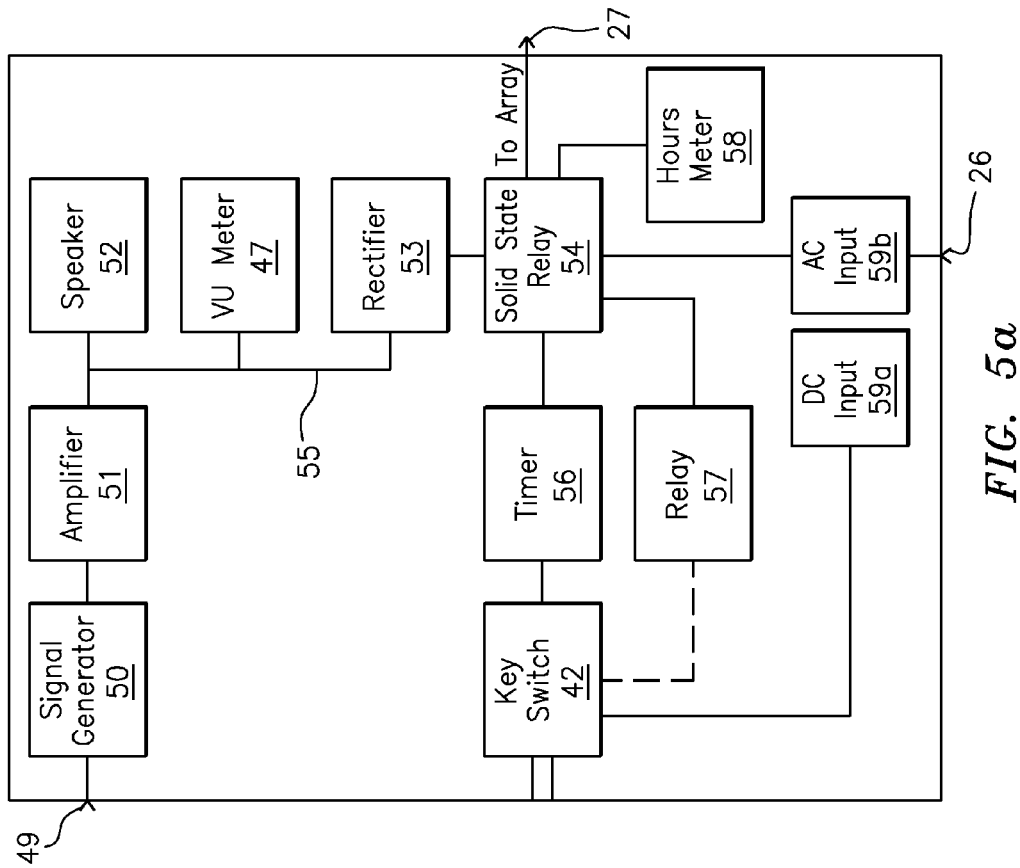
FIG. 5a is a schematic block circuit diagram of the controller of the fat reducing device utilizing optical emitters in accordance with one embodiment of the invention.

FIG. 5a illustrates one embodiment of a circuitry block diagram of the controller 40 described above. As shown, the internal components can include, for example, a signal generator 50, an amplifier 51, one or more speakers 52, a rectifier 53, one or more solid state relays 54, a timer 56, a control switch relay 57, an hours meter 58, an AC power input device 59b, and a DC power module 59a. Each of these components and the user interfaces described above can be communicatively linked via one or more internal cables 55, bus or other suitable device. The controller 40 can be manufactured in accordance with any number of known construction methodologies, and one or more of the internal components, although listed as separate elements, can be formed together to form a printed circuit board or other such component, for example, in accordance with known manufacturing processes.

The main body 41 can act to securely position each of the elements 42-59 in secure manner so as to form a single unit which can be operated by a user. The body itself can take any number of distinct shapes and sizes, and can be constructed from any number of known materials such as plastic or metal, for example. Of course, other known materials and manufacturing processes are also contemplated.

The key switch 42 can function to provide security against operation of the device by unauthorized persons. To this end, the key switch can interface with a physical key and an internal relay 57 to switch the device between a plurality of operating states. For example, the key can switch the device between: on with internal modulation selected, device off, and device on with external modulation source selected. Although illustrated herein as using a physical key, other access control devices can also be utilized herein. Several non-limiting examples including: key fob, access code (via an integrated keypad), biometric sensors and the like.

The stop button 43 can function to immediately cease power distribution to the array 30 when engaged. The speaker volume selector 44 can comprise a switch or knob, for example, which acts to control the output of the one or more speakers 52. The exposure time selector 45 can comprise a switch or knob, for example, which can allow a user to specify how long power will be sent to the array during a particular treatment. The array indicator 46 can include a light or other such notification instrument suitable for notifying a user when power is being sent to the array.

The modulation signal strength indicator 47 can act to indicate the presence of an external modulation signal, and to display a visual representation of the signal to a user. The visual representation also indicating the delivery of power to the array 30. The start button 48 functions to initiate the device timer 56 and allows power to be sent to the array 30.

One or more input jacks 49 can be provided to allow the controller 40 to interface with an external device such as a computer/tablet device, radio, television, CD player, DVD player, or MP3 player, for example. These external devices can generate and transmit an audio or sub audio input signal i.e., reference waveform such as music or words, for example, to the controller 40. In one preferred embodiment, the input jack 49 can include a standard ⅛ inch modulation input jack (e.g., mini-phone plug) and/or other forms of input devices such as a USB port, for example.

The input jack 49 can be connected to the internal signal generator 50 such as an audio oscillator, for example, which can act to either generate or pass through the received reference waveform.

In operation, the controller 40 can be connected to a conventional 120V AC input source, which can supply power to the internal DC module 49 for powering the controller interfaces. The received AC power can also be modulated and subsequently transferred to the array 30 which can utilize the same to generate an optical output. The controller 40 and/or array 30 can also include any number of fuses to protect the recipient, operator and device in the event of an electrical problem or excessive current flow through the device components. The flow of electricity (120 VAC) to the array 30 can be controlled by the timer circuit 56, which can interface with the start button 48, stop button 43, the exposure time selector 45 and the array indicator 46.

Together with array positioning relative to the client's body, the controller 40 can vary the fluency of the photonic energy delivered to the skin and underlying tissue. The start button 48 begins the timer circuit 56, which allows power to be sent to the array 30 for conversion into light via the plurality of optical emitters 32. When the array is illuminated, the hours meter 58 advances to record the total operation time of the device.

The controller 40 can execute a method to control the fluency by modulation of the current transmitted to the optical emitters 32 of the array 30. In one embodiment, the current to the array 30 can vary based on the frequency of the reference waveform (i.e., audio input signal) that is internally generated 50 or that is generated by an external device and connected to the input jack 49.

Figure 6A:
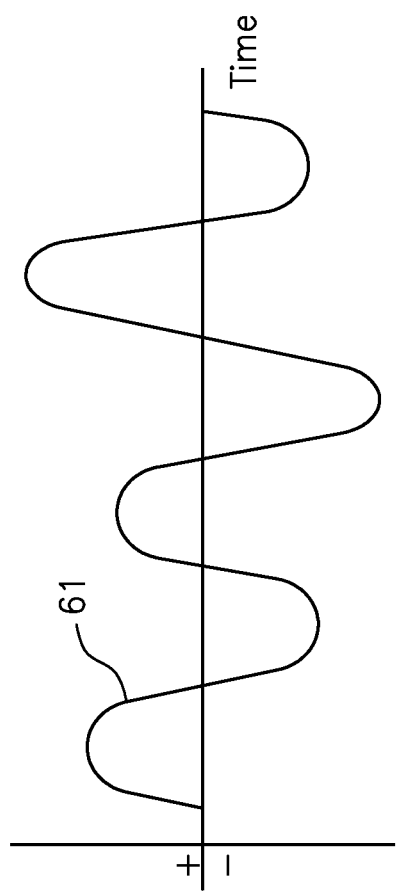
Figure 6B:
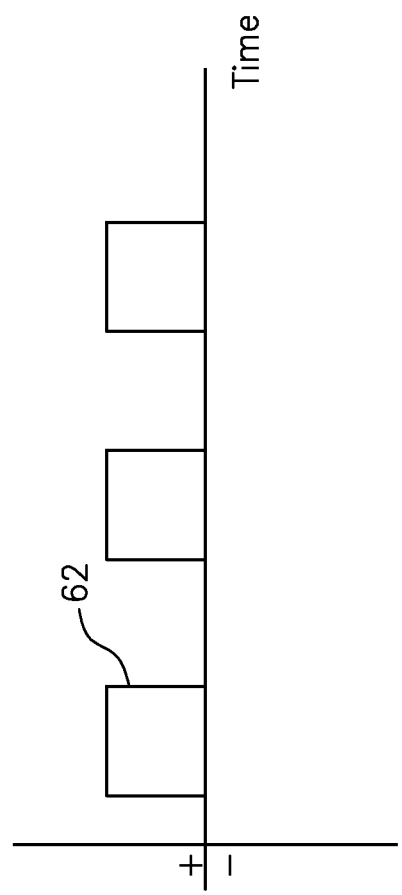

The reference waveform 61 (see FIG. 6a) can be supplied to the amplifier 51 before being sent to the rectifier 53. The rectifier can function to produce an output voltage representing only the positive portion of the reference waveform. This output voltage 62 (See FIG. 6b) can function to activate the Solid-State Relay (SSR) 54, and the negative portion is shunted to ground. As such, when the SSR is active, 120V AC power can be passed to the array 30 for conversion into light via the plurality of optical emitters 32. Alternatively, when the output voltage 62 is not present, or drops below a predetermined threshold, the SSR can prevent the 120V AC power from passing to the array 30 until the next positive cycle of the reference signal 61. As such, modulation of the array output is accomplished by varying the current and pulse width of the 120V AC voltage supplied to the array 30 from the controller 40.

The VU Meter 47 can be in communication with the signal generator and rectifier in order to provide a visual indicator of the input frequency strength for purposes of adjustment. The audio amplifier 51 can also provide the input signal to the speaker 52 so as to allow the operator to simultaneously listen to the input signal. Each of the amplifier and speaker can be controlled by the volume selector 44 in order to vary the volume of the monitored input signal.

The content of the audio input signal controls the array fluency with respect to time, affecting and controlling the photonic energy delivered to the skin and underlying tissue. A different audio recording (or video recording with sound) will result in the array having a different fluency and excitation patterns with respect to time, which further results in varying photochemical and biochemical responses and outcomes at a cellular level. By providing a means for communicating with an external device, the controller 40 can allow an operator maximum flexibility for generating a virtually unlimited number of array fluencies through modulation of various audio input signals.

Modulation will optimize the results, but is not required for lipolysis to occur. To this end, the device 20 can be operated without modulation, wherein the controller 40 can provide a constant and steady power source to the array 30 for a specific period of time.

Figure 5B:
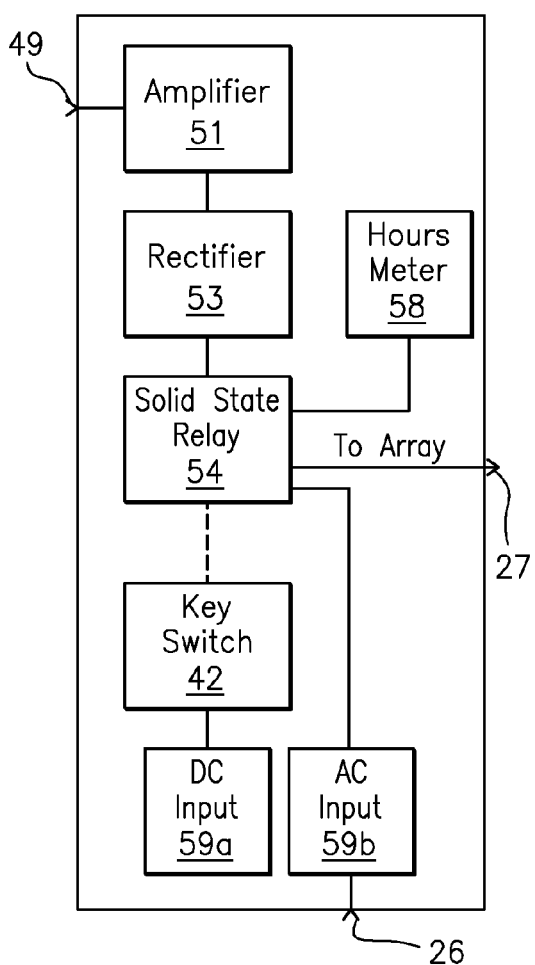
FIG. 5b is a schematic block circuit diagram of the controller of the fat reducing device utilizing optical emitters in accordance with another embodiment of the invention.
Figure 4B:
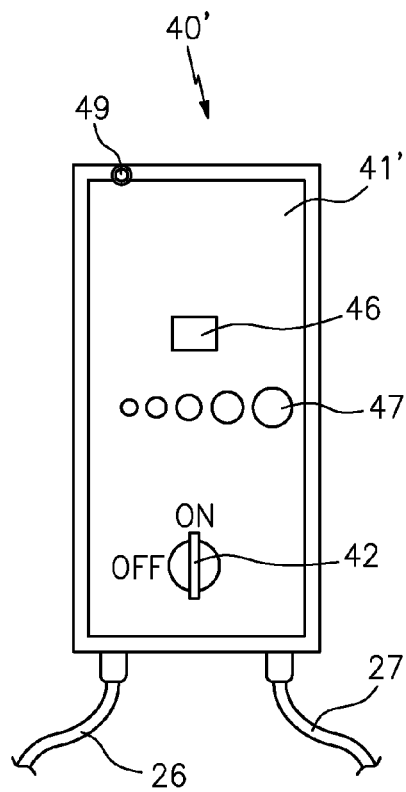
FIG. 4b is a perspective view of the controller of the fat reducing device utilizing optical emitters in accordance with another embodiment of the invention.

Although described above with respect to particular components, those of skill in the art will recognize that the inventive concepts disclosed herein can be accomplished by substituting certain components for other functionally equivalent components, or by reducing the number of components into a more simplified controller. To this end, FIGS. 4b, and 5b, illustrate but one possible alternative embodiment of a controller for operating the array 30.

As shown, controller 40' can also include a main body 41', having one or more user controls and/or interface devices secured thereon. These devices can also include a key switch 42, an array indicator 46, a modulation signal strength indicator 47, and a signal input jack 49. Of course any number of other interface devices can also be provided. As shown by the exemplary circuitry block diagram, the controller 40' can include, for example, an amplifier 51, a rectifier 53, one or more solid state relays 54, an hour meter 58, an AC power input 59b, and a DC power module 59a.

In the present embodiment, the key switch 42 functions to replace the start button and the stop button. In this regard, when the key switch is in the on position, the controller 40' provides power to the array 30 based on a reference waveform received by the input jack 49, as described above. Conversely, when the key is in the off position, no power is sent to the array, and the DC power to the controller components is disabled. Such a feature can allow the size of the controller to be small in nature, typically between about 14 and 20 inches, so as to enable the device to be easily transported.

Figure 7:
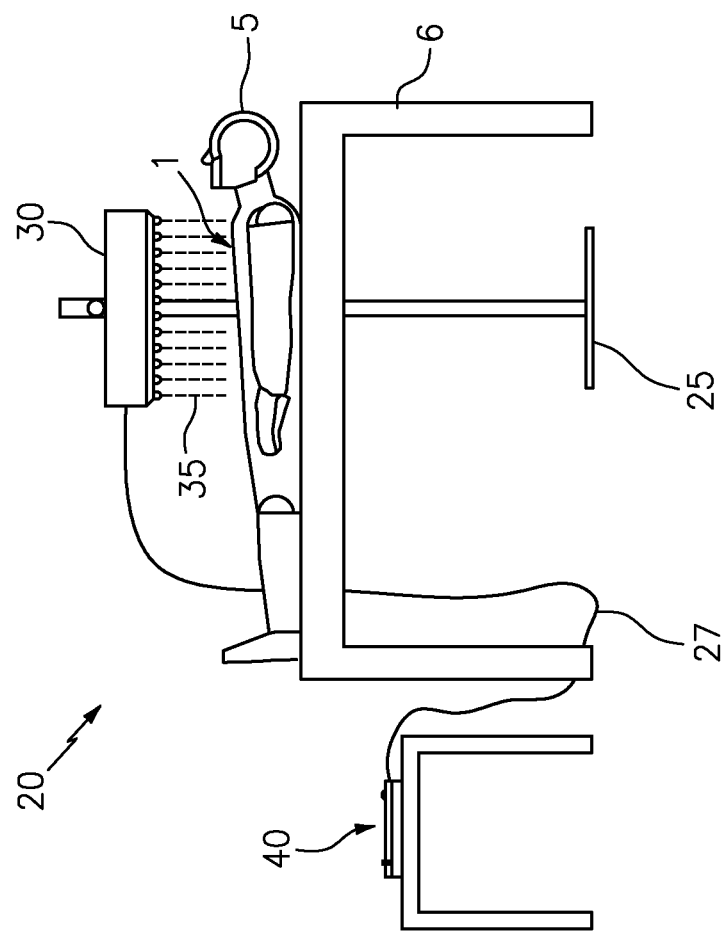
FIG. 7 is a perspective view of the fat reducing device utilizing optical emitters in operation, and in accordance with one embodiment of the invention.

FIG. 7 illustrates one embodiment of the fat reducing device utilizing optical emitters 20 in operation to treat a recipient. As shown, the recipient 5 can be positioned on a table 6 or other suitable platform, and the array 30 can be positioned above the target area 1 of the recipient via the stand 25.

In one preferred embodiment, the array can be positioned between about 1 and 8 inches from the target area of the recipient and an operator (not shown) can utilize the controller 40 to activate the array. Once activated, the optical emitters of the array can produce the optical output 35 described above that is sufficient to allow approximately 313.6 Lux to be delivered to the subcutaneous adipocytes of the target area for a period of about 1 to 8 minutes.

Although the above described procedure represents the preferred embodiment for weight loss, those of skill in the art will recognize that when the dosimetry is lowered to the recipient 5 via moving the device away from the surface of the skin 1, longer exposure times may be necessary to produce optimal results. Likewise, when the device is placed closer to the skin, resulting in higher dosimetry, shorter exposure times may be necessary to produce optimal results. In this regard, and in accordance with one method of operation, the effective operating range of the device 20 for weight loss is between about 1 to 10 inches, and a maximum operating time of between 1 and 10 minutes, respectively.

In addition to weight loss, the device 20 can also be utilized for other therapeutic treatments such as collagen and elastin production, for example. When utilized for these treatments, results have been achieved at distances between the array 30 and the target area 1 of about 1 and 18 inches, and for operating times of between about 1 and 120 minutes, for example.

Figure 8:
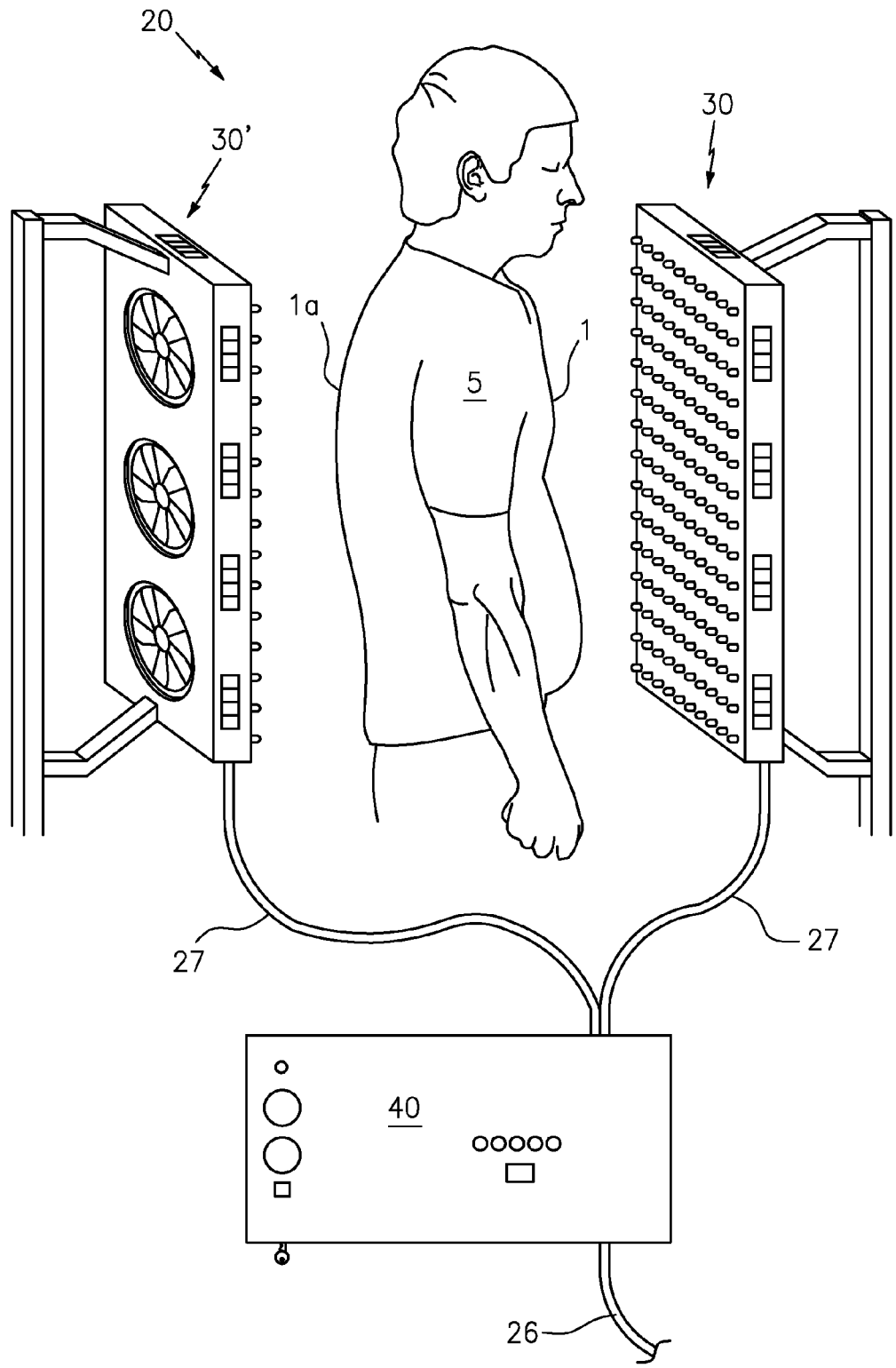
FIG. 8 is a perspective view of the fat reducing device utilizing optical emitters in operation, and in accordance with an alternate embodiment of the invention.

Although described above with reference to a single controller and a single array, other embodiments are also contemplated. FIG. 8 illustrates an alternate embodiment of the device 20 wherein a plurality of arrays 30 and 30' function in unison to treat multiple target areas 1 and 1a of a recipient 5 simultaneously. As described herein array 30' can be constructed in an essentially identical manner as array 30 described above, and each of the arrays can be tethered 27 to a single controller 40. In this regard, the device 20 can also function to treat multiple areas of a single recipient at one time.

Figure 9:
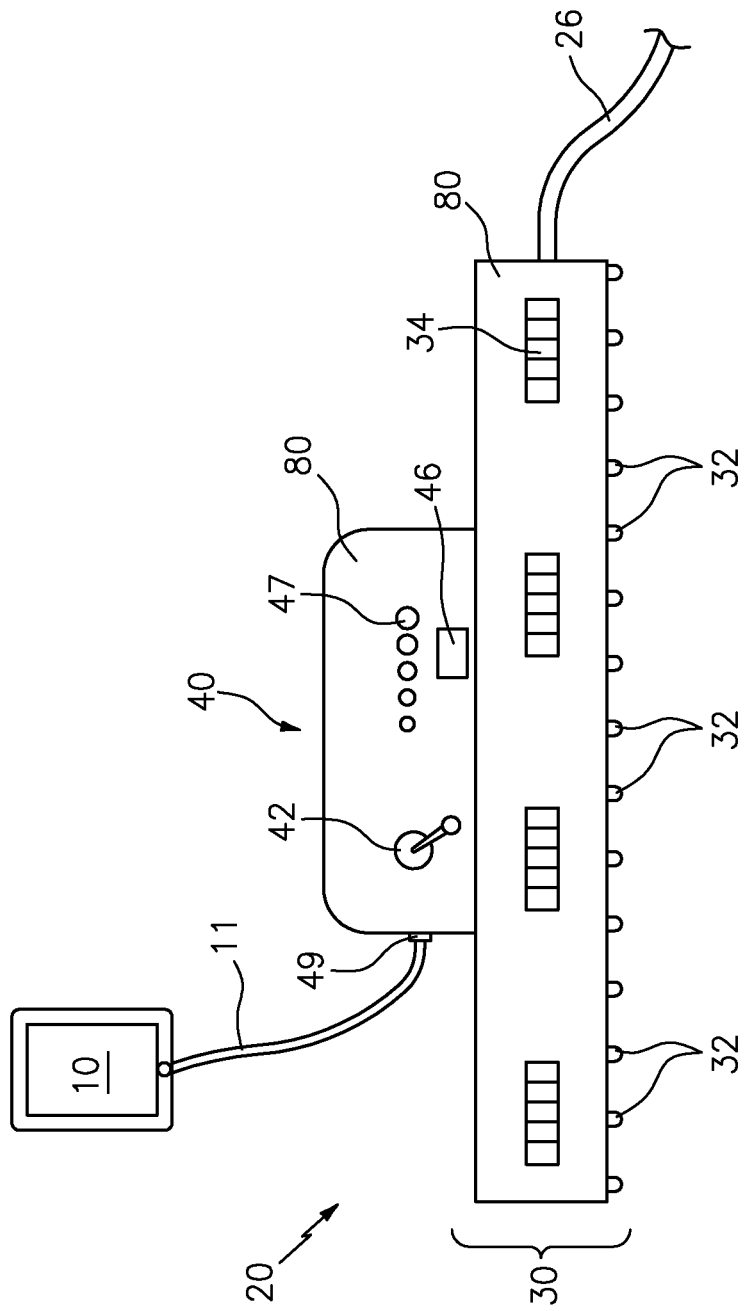
FIG. 9 is a perspective view of the fat reducing device in accordance with another alternate embodiment of the invention.

FIG. 9 illustrates yet another embodiment of the device 20, wherein the controller 40 and array 30 are integrated into a singular structure. In the present embodiment, the controller main body 41 and the array main body 41 are joined to create a unified main body 90 that houses the controller and array components as heretofore described. As shown, the device 20 can be connected to an external device 10 (in this instance a tablet pc) via an audio cable 11 in order to receive the audio signal.

By providing a more simplified array and controller, as described above, the device can operate in self-service capacity. To this end, the user interfaces of the controller can be accessible to a recipient at all times during treatment. Such a feature can allow the recipient/end user to control the physical operation of the device at all times, thereby ensuring compliance with any jurisdictional laws or regulations regarding the operation of such equipment by anyone other than the end user/recipient. In this regard, the device will preferably be equipped with only the on/off switch, however any number of other user interfaces can also be provided.

When following the recommended protocol, the advantages of the present invention may include, without limitation, the stimulation of biochemical processes of lipolysis and other desirable effects in the adipocyte, which could lead to reversals not only of obesity, but decrease unpleasant and harmful side effects of obesity, such as diabetes and high blood pressure, and heart attack. The benefits may also include the stimulation of production of collagen, elastin, leptin, and adiponectin. The ease of fat reduction can cause a drop in the BMI of obese individuals. As obese people suffer from many more medical conditions, thereby overburdening the healthcare system of the U.S. and other countries, lessening the number of people who suffer from obesity will undoubtedly be a large advantage to society financially as well as result in reduced number of people suffering from severe and potentially debilitating and life changing medical conditions.

In addition, the noninvasive, non-painful, and generally risk-free method is much more beneficial to the body than a surgical method of fat reduction. Many obese individuals at risk of diabetes and heart conditions are not surgical candidates; furthermore, surgical methods of localized fat reduction have not been shown to reduce the risk of heart disease, diabetes, or other weight-related medical conditions.

As described herein, one or more elements of the controllers 40 and 40' and the arrays 30 and 30' can each be constructed utilizing any number of known means of attachment such as, for example, screws, glue, compression fittings and welds, among others. Moreover, although various components may be described herein as including separate individual elements, other embodiments are contemplated wherein multiple individual components are formed together as one continuous element, either through manufacturing processes, such as welding, casting, or molding, or through the use of a singular piece of material milled or machined with the aforementioned components forming identifiable sections thereof.

As to a further description of the manner and use of the present invention, the same should be apparent from the above description. Accordingly, no further discussion relating to the manner of usage and operation will be provided.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A device for applying optical emissions to a recipients body, said device comprising:
   an output array that includes
      a main body having a first surface which may be oriented toward and positioned a first distance from, a target area of a recipient to be treated,
      a plurality of optical emitters disposed within the main body such that an optical emission from each of the emitters is directed outward from the first surface; and
   a controller that is in communication with the array, said controller including
      a plurality of user interface devices for instructing an operation of the array and for transitioning the array between an on-position and an off-position, wherein in the on-position, the array produces an optical output of red light at approximately 635 nm, and at approximately 40,000 Lux, to reduce a lipid content of adipocytes in the target area of the recipient, and
      an internal signal generator for creating a reference waveform, a power input module, a rectifier and a solid state relay, said rectifier and relay functioning to provide a modulated power output to the array based on the created reference waveform, said rectifier and relay further functioning to provide the power output to the array only during a positive portion of the created reference waveform.

2. The device of claim 1, wherein each of the plurality of optical emitters comprise, at least one of, a light emitting capacitor, a light emitting diode, and a super-luminous light emitting diode.

3. The device of claim 1, wherein the plurality of optical emitters include 150 2-Watt LEDs having an output spectrum of approximately 635 nm.

4. The device of claim 1, wherein the controller is integrated into the main body of the output array.

5. The device of claim 4, wherein the user interface devices of the controller are positioned to allow the recipient to operate the device in a self-service capacity.

6. The device of claim 1, wherein the first distance is between 1 and 8 inches, and in the on-position, the array produces red light at approximately 635 nm and at about 313.6 Lux measurable at a subcutaneous location of the target area of the recipient.

7. The device of claim 1, wherein the target area includes a dimension of about 23 inches by 17 inches measurable on the recipient.

8. The device of claim 1, further comprising:
   a second output array that is also in communication with the controller,
   said second array including first surface which may be oriented toward a second target area of the recipient to be treated, and producing an optical output of red light at approximately 635 nm, and at approximately 40,000 Lux.

9. A device for applying optical emissions to a recipients body, said device comprising:
   an output array that includes
      a main body having a first surface which may be oriented toward and positioned a first distance from, a target area of a recipient to be treated,
      a plurality of optical emitters disposed within the main body such that an optical emission from each of the emitters is directed outward from the first surface; and
   a controller that is in communication with the array,
      said controller including a plurality of user interface devices for instructing an operation of the array and for transitioning the array between an on-position and an off-position,
      an input jack for receiving a reference waveform from an external device,
      a power input module,
      a rectifier, and
      a solid state relay, said rectifier and relay functioning to provide a modulated power output to the array based on the received reference waveform, said rectifier and relay further functioning to provide the power output to the array only during a positive portion of the created reference waveform, wherein in the on-position, the array produces an optical output of red light at approximately 635 nm, and at approximately 40,000 Lux, to reduce a lipid content of adipocytes in the target area of the recipient.

* * * * *